United States Patent [19]

Ishikawa et al.

[11] Patent Number: 5,090,808

[45] Date of Patent: Feb. 25, 1992

[54] PARTICLE MEASUREMENT APPARATUS

[75] Inventors: Muneharu Ishikawa, Ryuugasaki; Ayafumi Taniji, Tsukuba, both of Japan

[73] Assignee: Kowa Company Ltd., Japan

[21] Appl. No.: 435,717

[22] Filed: Nov. 13, 1989

[30] Foreign Application Priority Data

Nov. 16, 1988 [JP] Japan .................................. 63-287809

[51] Int. Cl.⁵ ...................... G01N 15/02; G06M 11/04
[52] U.S. Cl. .................................... 356/336; 356/338; 356/343; 377/11; 250/574
[58] Field of Search ............................... 356/335-343, 356/39; 250/574, 576, 564; 377/11, 10

[56] References Cited

U.S. PATENT DOCUMENTS

| | | | |
|---|---|---|---|
| 3,094,625 | 6/1963 | Hendrick | 356/336 |
| 3,705,771 | 12/1972 | Friedman et al. | 356/39 |
| 4,021,117 | 5/1977 | Gohde et al. | 356/335 |
| 4,401,387 | 8/1983 | Tokinage et al. | 356/343 |
| 4,595,291 | 6/1986 | Tatsuno | 356/336 |
| 4,613,938 | 9/1986 | Hansene et al. | 356/336 |
| 4,830,494 | 5/1989 | Ishikawa et al. | 356/336 |
| 4,942,305 | 7/1990 | Sommer | 356/339 |

*Primary Examiner*—Richard A. Rosenberger
*Assistant Examiner*—Hoa Pham
*Attorney, Agent, or Firm*—Bruce L. Adams; Van C. Wilks

[57] ABSTRACT

A particle measurement apparatus is disclosed in which a laser beam is projected at a sample containing particles to be measured in a measurement zone and light scattered by particles in the sample is evaluated to thereby determine properties of particles in the sample. The apparatus includes a plurality of light receiving systems for receiving scattered light arranged at different angles relative to the axis of the laser beam. The amplitude of scattered light signals from the light receiving systems are compared with predetermined values. The arrangement is such that particles are counted by size only when the scattered light signals from the light receiving systems exceed a predetermined value, enabling false signals caused by noise and the like to be eliminated and assuring more accurate measurements.

14 Claims, 2 Drawing Sheets

PARTICLE MEASUREMENT APPARATUS

BACKGROUND OF THE INVENTION

1. Field of the Invention

This invention relates to a particle measurement apparatus, and more particularly to a particle measurement apparatus in which a laser beam is projected at a sample in a measurement zone and light scattered by particles in the sample is evaluated to thereby measure properties of particles in the sample.

2. Description of the Prior Art

Optical measurement apparatuses in conventional use include those employing scattered light to measure particles in a liquid or gaseous medium in which the concentration of the particles in the medium is very low, so that only one or two particles traverse the measurement zone at one time. The object of such apparatuses is to measure particle size and other such properties by using a sensor to evaluate the scattering of the light projected at the liquid or gas concerned. Conventionally, these scattered light type particle measurement apparatuses usually employ a laser light source. A laser light source provides a light beam that can be converged to a fine beam at the focal point. In such an arrangement, the energy density can be increased at the location where the illuminating beam is focussed, thus enabling the measurement of particles as small as 0.1 micrometers to (see, for example U.S. Pat. No. 4,830,494).

With this type of particle measurement apparatus that utilizes a laser light source, the laser beam is projected at a measurement zone through which the gaseous or liquid sample flows, the scattered light is measured at a predetermined angle relative to the direction of incidence of the laser beam and converted to electrical signal pulses by a photoelectric converter. The output signals are then discriminated in terms of a pulse height, and counted by an internal counter corresponding to a predetermined size to measure the number of the particles that have the predetermined size.

However, the intensity of a laser beam produced by a single mode laser has a Gaussian distribution in a plane, normal to the beam axis. Thus, if the center of light intensity is $I_O$, the relationship between the intensity I and the distance from the center r is expressed by $$I = I_O e^{-2(r/rO)2}$$

($r_O$ being r when $I = I_O e^{-2}$). Therefore, the intensity of scattered light from particles passing through the laser beam will vary according to the position of the particle. Thus, the intensity of the scattered light from the particles will not be the same even when the particles concerned are the same size. Instead, scattered light from a particle passing through a region of high light intensity will have a high intensity and scattered light from a particle passing through a region of low light intensity will have a low intensity, resulting in the same sized particles being counted as particles of different sizes.

To avoid this, as explained below, there is a measurement method comprising the steps of arranging a plurality of light receiving systems at different angles with respect to the axis of the laser beam, finding the ratios of the scattered light intensities obtained from the light receiving systems, and determining the particle size on the basis of the relationship between the scattered light intensity ratios and particle size.

In such an arrangement, there are provided a first light receiving lens that receives scattered light at a forward angle of 6 degrees to the laser beam axis and a second light receiving lens that receives scattered light at a forward angle of 3 degrees to the laser beam axis. The scattered light in each case is detected by a photosensor and converted to electrical signals which are amplified by an amplifier circuit. A divider is used to obtain the ratio of the scattered light intensities. In accordance with Mie's scattering theory, as described below, there is a predetermined relationship between particle size and the ratio, of the scattered light intensities; Thus, the particle size can be determined based on this predetermined relationship.

However, when such an arrangement is used that includes two light receiving lenses to detect scattered light at different angles, there is a discrepancy between the fields of view of the lenses. As a result, a scattered light signal from a particle may be received from one of the light receiving lenses but not from the other. This would not present a problem if there were a complete absence of a scattered light signal from one of the light receiving systems, but if even a small amount of noise should intrude into the light receiving system, there is a risk that the ratio of the noise to the signal from one of the light receiving systems may be wrongly interpreted as being the ratio of scattered light intensities produced by a particle.

Also, when a signal is received that exceeds the dynamic range of the light receiving systems, there is a risk that the ratio of the saturated values may be included in the particle count.

SUMMARY OF THE INVENTION

It is therefore an object of the present invention to provide a particle measurement apparatus which can prevent an erroneous measurement of particle sizes caused by a disparity between measurement fields of view when an using a plurality of light receiving systems to determine particle size from the ratio between the scattered light intensities detected by the systems.

It is another object of the present invention to provide a particle measurement apparatus which can prevent an erroneous measurement of particle sizes caused by the reception of signals that exceed the dynamic range of the light receiving systems.

According to the invention, a particle measurement apparatus is provided in which a laser beam is projected at a sample containing particles to be measured in a measurement zone and light scattered by particles in the sample is evaluated to determine properties of particles in the sample. The apparatus comprises a plurality of light receiving systems for receiving scattered light arranged at different angles relative to the axis of the laser beam, means associated with each of the light receiving systems for converting the scattered light into an electrical scattered light signal, means for processing the scattered light signals from the light receiving systems to determining particle size, and means for comparing the amplitude of scattered light signals from the light receiving systems with predetermined values. In this arrangement, a particle measurement takes place only when a scattered light signal from each light receiving system exceeds a predetermined value.

In accordance with the above arrangement, means are provided for comparing the amplitudes of the scattered light signals from the light receiving systems with predetermined values, and a particle measurement only takes place when scattered light signals from the light receiving systems exceed predetermined values. This enables erroneous particle counts to be excluded that are caused when only noise comes from one of the light receiving systems, instead of a signal, so that only particles that pass through the same fields of view of the two light receiving systems are subjected to particle size measurement and counted according to its size, thus enabling accurate particle measurement.

BRIEF DESCRIPTION OF THE DRAWINGS

The objects and features of the present invention will become more apparent from the following detailed description taken in conjunction with the accompanying drawings, in which.

DETAILED DESCRIPTION OF THE PREFERRED EMBODIMENTS

Figure 1:
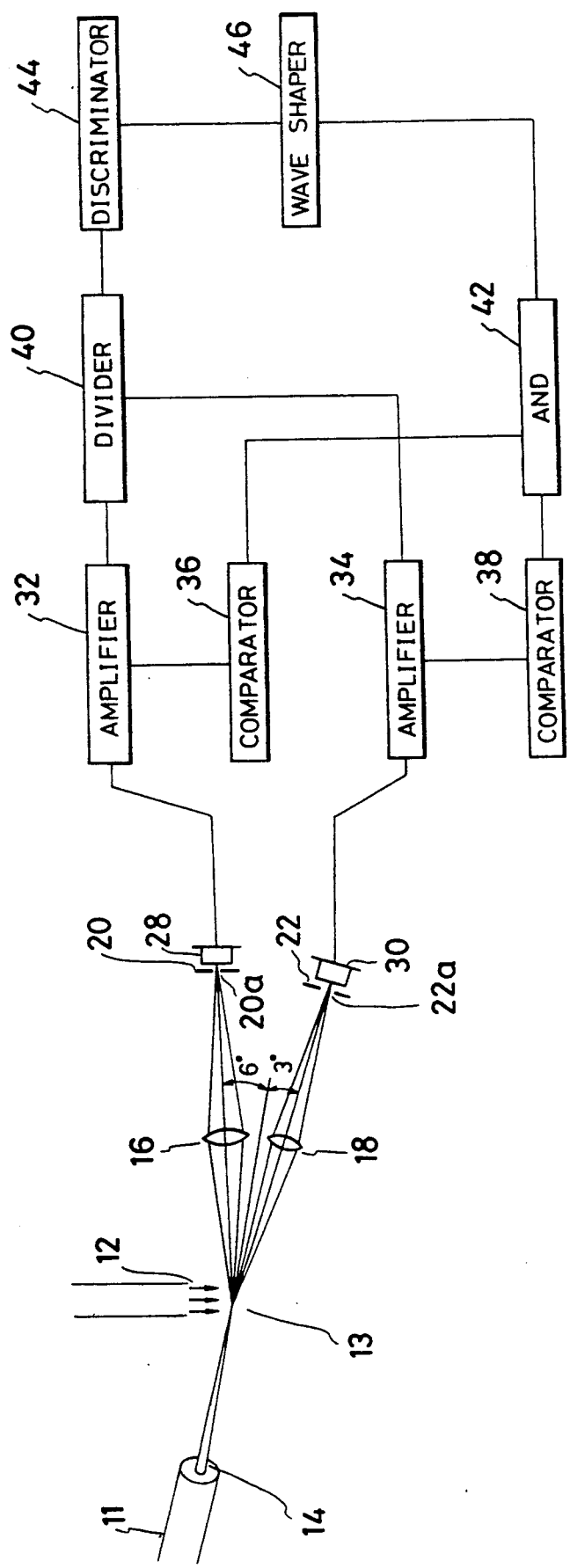
FIG. 1 is a schematic view showing the basic arrangement of a particle measurement apparatus according to the present invention.

The invention will be described in detail in connection with embodiments shown in the drawings.

The invention is intended to provide a particle measurement apparatus in which a sample containing the particles to be measured is caused to flow through a measurement cell, and light scattered is detected from particles that pass through a particle detection zone formed by an incident laser light beam. FIG. 1 shows the basic arrangement of the apparatus according to the invention.

With reference to FIG. 1, a laser beam 14 produced by a laser light source 11 is used to illuminate a measurement zone 13 in a measurement cell (not illustrated) through which a sample containing particles 12 to be measured is caused to flow. Arranged at the laser beam exit side of the measurement cell are a first light receiving lens 16 and a second light receiving lens 18, which are positioned at an angle of, for example, 6 degrees and 3 degrees, respectively, relative to the axis of the laser beam.

Provided behind the first light receiving lens 16 and second light receiving lens 18 are masks 20 and, respectively, and 22 in which there are formed slits 20a and 22a respectively to limit the scattered light and define the measurement zone 13 to improve the signal to noise (S/N) ratio of the light after is converted to an electrical signal. Provided to the rear of the masks 20 and 22 are photoelectric converters 28 and 30, respectively which are constituted by photomultipliers, for example.

The photoelectric converters 28 and 30 are connected to amplifiers 32 and 34. One of the outputs of the amplifier circuit 32 is connected to the input of a comparator circuit 36 and one of the outputs of the amplifier circuit 34 is connected to the input of a comparator circuit 38. The other outputs of the amplifiers 32 and 34 are connected to a common divider 40. The outputs of comparator circuits 36 and 38 are connected to the input of a common AND circuit 42. A wave height discriminator 44 is connected to the output side of the divider 40. The wave height discriminator 44 is also connected, via a waveform shaper 46, to the output terminal of the AND circuit 42.

The operation of the apparatus of the invention thus configured will now be described. A sample containing particles 12 to be measured flows through a measurement cell (not illustrated). When the particles 12 are illuminated by the laser beam 14 from the laser light source 11, the first light receiving lens 16 and second light receiving lens 18 converge the light scattered by the particles 12 to form an image at the masks 20 and 22, respectively. The scattered light limited by the slits 20a and 22a in the masks 20 and 22 impinges on the photoelectric converters 28 and 30 and is converted into electrical signal pulses which are then amplified by the amplifiers 32 and 34.

The pulse height values of the signals obtained from the photoelectric converters correspond to the intensity of the scattered light, enabling particles to be determined and counted after pulse height discrimination of the output signals of the photoelectric converters.

As mentioned, the intensity of a laser beam produced by a single mode laser has a Gaussian distribution in a plane normal to the beam axis, so that if the center of light intensity is $I_O$ the relationship between the intensity I and the distance from the center r is expressed by $$I = I_O e^{-2(r/r_0)^2}$$

Therefore, if $K_1$ is the scattered light intensity relative to a particle size at a forward angle of 6 degrees and $K_2$ is the scattered light intensity relative to a particle size at a forward angle of 3 degrees, the scattered light intensity ratio R will become $$R = \text{(scattered light intensity at a forward angle of 6 degrees)}/$$
$$\text{(scattered light intensity at a forward angle of 3 degrees)} =$$
$$\frac{K_1 I_O e^{-2(r/r_0)^2}}{K_2 I_O e^{-2(r/r_0)^2}} = \frac{K_1}{K_2}$$

and the influence of the position on the particles will be eliminated.

Figure 3:
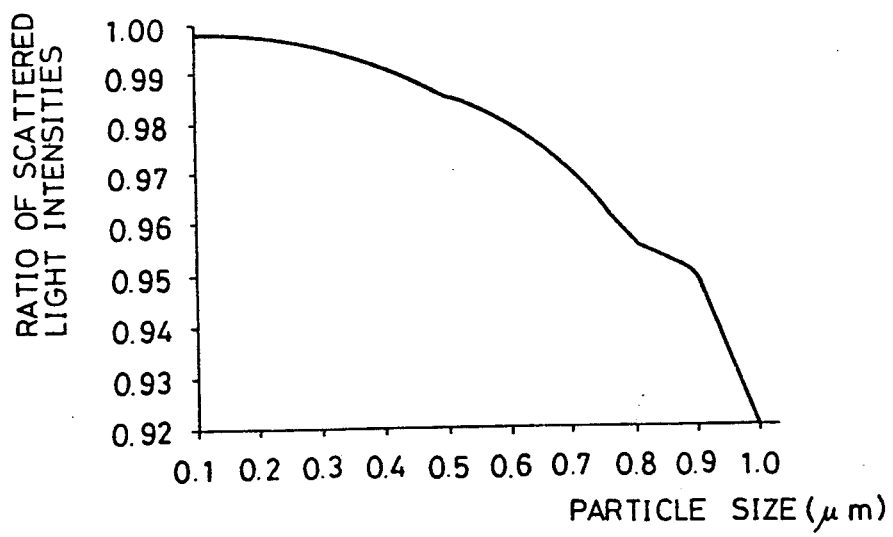
FIG. 3 is a graph showing the relationship between ratios of scattered light intensities and particle size.

In accordance with Mie's scattering theory, the relationship shown in FIG. 3 will obtain between particle size and the scattered light intensity ratio $K_1/K_2$, therefore, the size of a particle can be determined from FIG. 3. The vertical axis of the graph represents the above ratio R; the values shown are for a relative refractive index of 1.592.

Figure 2:
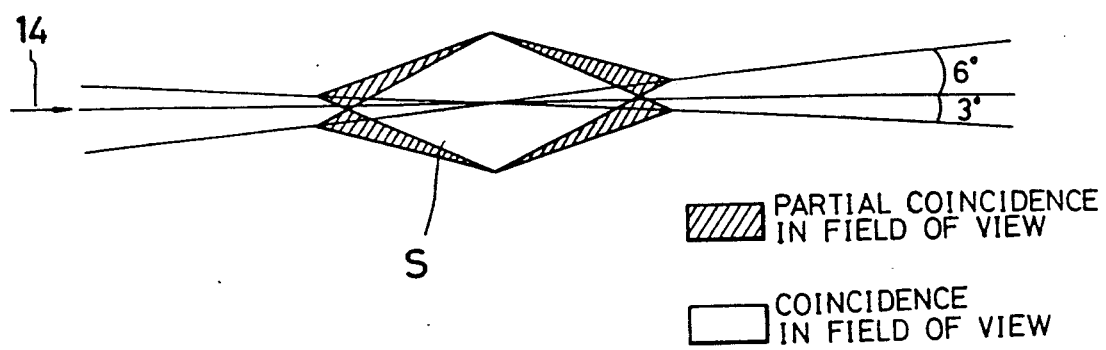
FIG. 2 is an explanatory view showing a discrepancy between the fields of view of multiple light receiving systems.

Assume that the effective F-number of the first light receiving lens 16 and second light receiving lens 18 is 2 and the diameter of the slits 20a and 22a is 100 micrometers. The fields of view of the light receiving lenses 16 and 18 will be as shown in FIG. 2, with one portion partly out of mutual alignment (the hatched portion). Therefore, when a particle light passes through the part where the fields of view do not coincide, one of the scattered light intensities will become zero, or will become a noise value if there is noise present. In order to prevent the ratio between the other scattered light signal and a noise signal from being taken as that derived from the scattered light intensities produced by a particle, there are the comparator circuits 36 and 38 connected to the amplifiers 32 and 34. The comparator circuits 36 and 38 contain respective predetermined upper and lower threshold values which form the criteria for particle recognition. The lower threshold values are respectively predetermined to be slightly greater than a noise level of the respective amplifiers 32 and 34. The upper threshold values are respectively predetermined to be slightly less than the dynamic range of the respective amplifiers 32 and 34.

The scattered light intensity signals converted by the photoelectric converters 28 and 30 are amplified, and are fed to the divider 40 to derive a ratio between signals received via the first light receiving lens 16 and signals received via the second light receiving lens 18, i.e. the scattered light intensity ratio R.

The outputs of the amplifiers 32 and 34 are also input into the comparator circuits 36 and 38 where they are each compared with the predetermined upper and lower threshold values. Only signals that are within these limits are then input to the common AND circuit 42. Only when the signals from both the amplifiers are input to the AND circuit 42, meaning only when the signals are from a particle that has passed through the common field of view S shown in FIG. 2, the AND circuit 42 produces an output signal, which is fed to the waveform shaper 46. In response to the output signal from the AND circuit 42, the waveform shaper 46 removes noise from the edges of the AND output signal and produces a signal having a predetermined width, which is output to the wave height discriminator 44. The wave height discriminator 44 only operates when it receives the output signal from the waveform shaper 46, and, based on a discrimination of the output signal from the divider 40 by wave height values, the particles are discriminated in terms of particle size and counted by an internal counter for each particle size. As the wave height discriminator 44 thus operates only during the time the AND circuit 42 is producing an output, a pulse count is effected by the wave height discriminator 44 only when a particle producing a signal amplitude within the prescribed limits passes through the field of view common to the two light receiving systems.

As, moreover, each of the comparator circuits 36 and 38 contains upper and lower threshold values, signals that exceed the dynamic range of the light receiving systems can be excluded.

Although the above-described embodiment uses two light receiving lenses, it is to be understood that the same object can be attained using three or more such lenses.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. A particle measurement apparatus in which a laser beam is projected at a sample containing particles to be measured in a measurement zone and light scattered by particles in the sample is evaluated to thereby determine properties of particles in the sample, comprising:
    a first light receiving system for receiving scattered light and disposed at a predetermined angle relative to the axis of the laser beam;
    a second light receiving system for receiving scattered light and disposed relative to the axis of the laser beam at an angle different from the angle of the first light receiving system;
    means associated with each of the light receiving systems for converting the scattered light into an electrical scattered light signal;
    means for processing the scattered light signals from the light receiving systems to determine particle size; and
    means for comparing the amplitude of scattered light signals from the light receiving systems with predetermined values so that a single particle measurement takes place only when a scattered light signal from each light receiving system exceeds a predetermined value.

2. The particle measurement apparatus according to claim 1, wherein a particle measurement takes place when a scattered light signal from each light receiving system exists between predetermined upper and lower threshold values.

3. The particle measurement apparatus according to claim 1, wherein a ratio between scattered light intensities is obtained to determine the particle size.

4. A particle measurement apparatus in which a laser beam is projected at a sample containing particles to be measured in a measurement zone and light scattered by particles in the sample is evaluated to thereby determine properties of particles in the sample comprising:
    first and second light receiving systems for receiving scattered light, said first light receiving system and said second light receiving system being arranged at different angles relative to the axis of the laser beam;
    first and second photoelectric converters for converting the scattered light from the first and second light receiving systems into an electrical scattered light signal, respectively;
    first comparator means for comparing the amplitude of the scattered light signal from the first photoelectric converter with predetermined upper and lower threshold values;
    second comparator means for comparing the amplitude of the scattered light signal from the second photoelectric converter with predetermined upper and lower threshold values;
    means for processing the scattered light signals from the first and second photoelectric converters to determine particle size for a single particle; and
    means for activating said processing means only when a scattered light signal rom each photoelectric converter lies between said respective predetermined upper and lower threshold values.

5. An apparatus according to claim 4, wherein said processing means comprise a divider for determining the ratio of the scattered light signals from the first and second photoelectric converters and a wave height discriminator connected to the divider for determining the particle size depending upon the wave height of the ratio signal from the divider.

6. A particle measurement apparatus in which a laser beam is projected along an axis at a sample containing particles to be measured in a measurement zone and light scattered by the particles is evaluated to thereby determine properties of the particles in the sample, comprising:
    first light-receiving means for receiving light scattered by particles in the sample and disposed at a predetermined angle relative to the axis of the laser beam;

second light-receiving means for receiving light scattered by particles in the sample and disposed relative to the axis of the laser beam at an angle different from the angle of the first light-receiving means;

converting means for converting the scattered light received by the first and second light-receiving means into corresponding electrical signal representative of the intensities of the scattered light; and means operative only when the electrical signals corresponding to the intensities of scattered light received by the first and second light-receiving means exceed a predetermined value for processing the electrical signals to determine particle size.

7. An apparatus according to claim 6; wherein the means for processing comprises a first comparator for comparing the amplitude of the electrical signal corresponding to the scattered light received by the first light-receiving means with a predetermined threshold value, and a second comparator for comparing the amplitude of the electrical signal corresponding to the scattered light received by the second light-receiving means with a predetermined threshold value.

8. An apparatus according to claim 6; wherein the means for processing includes means for processing the electrical signals to determine therefrom a ratio of intensities of scattered light received by the first and second light-receiving means, and means for discriminating the ratio to determine the particles size.

9. A particle measurement apparatus for measuring particles at a measurement zone, comprising: a laser light source for projecting a laser light beam at a particle contained at a measurement zone; at least two light-receiving means for receiving light scattered by the particle, each light-receiving means being disposed at a different respective angle relative to a longitudinal axis of the laser light beam; converting means for converting the scattered light received by each light-receiving means into a corresponding electrical signal; and processing means for comparing each of the electrical signals with a respective predetermined lower threshold value to determine if each of the electrical signals is above said respective predetermined lower threshold value, and if each of the electrical signals is above said respective predetermined lower threshold value then processing the electrical signals to determine the size of the particle.

10. A particle measurement apparatus according to claim 9; wherein the processing means includes means for comparing each of the electrical signals with a respective predetermined upper threshold value, and if each of the electrical signals is between its respective predetermined upper and lower threshold values then processing the electrical signals to determine the size of the particle.

11. A particle measurement apparatus according to claim 10; wherein the processing means comprises first and second amplifier circuits for amplifying corresponding ones of the electrical signals, and first and second comparator circuits for comparing the corresponding amplified electrical signals with their respective predetermined upper and lower threshold values, wherein each predetermined lower threshold value is dependent on a predetermined noise level of the corresponding amplifier circuit and each predetermined upper threshold value is dependent on a dynamic range of the corresponding amplifier circuit.

12. A particle measurement apparatus according to claim 11; wherein the processing means further comprises dividing means for determining a ratio of the electrical signals from the first and second amplifier circuits, and discriminating means for discriminating the ratio to determine the size of the particle.

13. A particle measurement apparatus according to claim 12; wherein the processing means further comprises an AND circuit receptive of an output from each comparator circuit for generating a measurement signal only when the electrical signals are between their respective lower and upper threshold values, and a wave shaping circuit receptive of the measurement signal for generating a pulse signal having a width corresponding to a time duration of a particle to be measured passing through the measurement zone.

14. A particle measurement apparatus according to claim 12; wherein each light-receiving means comprises at least one lens for focusing the scattered light on the converting means, each lens being disposed at a different respective angle relative to the longitudinal axis of the laser light beam.

* * * * *